United States Patent [19]

Schneider et al.

[11] 4,344,788

[45] Aug. 17, 1982

[54] METHOD OF PLANT GROWTH REGULATION

[75] Inventors: Louis Schneider, Elizabeth; David E. Graham, deceased, late of Westfield, both of N.J.; Fidelity Union Trust Company, Executor, Newark, N.J.

[73] Assignee: GAF Corporation, New York, N.Y.

[21] Appl. No.: 169,075

[22] Filed: Jul. 15, 1980
(Under 37 CFR 1.47)

[51] Int. Cl.³ .............................................. A01N 43/36
[52] U.S. Cl. ............................................ 71/76; 71/95
[58] Field of Search .......................... 71/95, 76, 118

[56] References Cited

U.S. PATENT DOCUMENTS

| | | | |
|---|---|---|---|
| 3,404,976 | 10/1968 | Olin | 71/76 |
| 3,475,155 | 10/1969 | Ishida et al. | 71/76 |
| 3,769,301 | 10/1973 | Olin | 71/95 |
| 4,013,444 | 3/1977 | Fridinger | 71/76 |
| 4,013,445 | 3/1977 | Bellus et al. | 71/76 |
| 4,153,446 | 5/1979 | Schneider et al. | 71/95 |
| 4,178,167 | 12/1979 | Schneider et al. | 71/95 |

*Primary Examiner*—Glennon H. Hollrah
*Attorney, Agent, or Firm*—James Magee, Jr.; Marilyn J. Maue

[57] ABSTRACT

The use of N-(haloacetyl)-N-(N'-methylenepyrrolidonyl)-2-alkoxyaniline compounds for regulating the natural growth or development of plants, particularly turfgrasses, is described herein.

2 Claims, No Drawings

METHOD OF PLANT GROWTH REGULATION

BACKGROUND OF THE DISCLOSURE

1. Field of the Invention

This invention relates to a method for regulating the natural growth or development of plants by means of chemical treatment. As employed herein, the term "natural growth or development" designates the normal life cycle of the plant in accordance with its genetics and its environment, in the absence of artifical, external influences. More particularly, this invention is concerned with a method wherein turfgrasses are treated with a chemical substance which serves to retard or reduce the rate of turfgrass growth.

2. Description of the Prior Art

U.S. Pat. No. 4,178,167 describes the use of compounds of this invention as herbicides in a procedure for inhibiting or destroying unwanted plants. It should be understood, however, that the regulation of natural growth or development discussed herein does not include herbicidal or killing action, and that the turfgrasses treated in accordance herewith are not unwanted plants.

Although lethal amounts of the materials disclosed herein might be employed to obtain destruction or total inhibition of certain plants, it is contemplated here to employ only such amounts of said materials as will serve to effectively regulate the natural growth or development in the desired manner. As long understood and well recognized by those skilled in the art, such effective plant regulating amounts will vary, not only with the particular material selected for treatment, but also with the regulatory effect to be achieved, the species of plant being treated and its stage of development, and whether a permanent or transient regulating effect is sought. Other factors which may bear upon the determination of an effective plant regulating amount include the plant growth medium, the manner in which the treatment is to be applied, and weather conditions such as temperature and rainfall.

The term "turfgrass" is generally considered as encompassing a variety of specialized grasses which are employed in the development and/or management of certain areas for specific purposes, such as utility, beautification and recreation. The use of a chemical treatment to reduce or retard the natural growth or development of turfgrass provides many advantages. Among the areas in which turfgrasses are most frequently used are roadbanks and medians which parallel long stretches of our highway system, the large grassy areas of golf courses and parks, the grounds which surround large educational or industrial institutions and, of course, the lawn of the homeowner. In all of such areas, it is readily apparent that a chemical treatment which serves to reduce or retard the rate of grass growth is highly desirable since it will serve to minimize the time and costs expended on maintenance. Such a treatment will also provide enchanced appearance by promoting more grass height uniformity and by suppressing unsightly seedhead development.

Growth retarding chemicals have been applied to turf since maleic hydrazide was introduced in 1949. Unfortunately, discoloration and thinning of turf often has accompanied growth suppression. Consequently, the use of retardant chemicals has largely been restricted to roadside and hazardous-to-mow areas. Chemicals with less phytotoxicity are necessary if the full potential of chemical growth retardation in turfgrass management is to be realized. Therefore, it is a particular object of the invention to provide a method of retarding the growth of turfgrass effectively without causing undesired discoloration or thinning of the turf.

SUMMARY OF THE INVENTION

In accordance with this invention, the desired retardation or reduction of the rate of growth of turfgrass is achieved by applying to turfgrass an effective amount of at least one compound of the formula N-(haloacetyl)-N-(N'-methylenepyrrolidonyl)-2-alkoxyanilines:

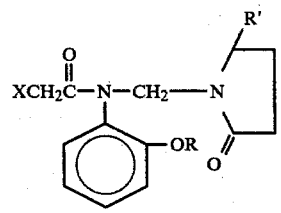

where
R is alkyl of 1–6 carbon atoms,
R' is hydrogen of lower alkyl of 1–3 carbon atoms, and;
X is halogen.

As employed herein, the term "alkyl" designates saturated aliphatic hydrocarbon radicals in a straight or branched chain.

Accordingly, typical compounds of the invention include N-(chloroacetyl)-N-(N'-methylenepyrrolidonyl)-2-methoxyaniline, N-(chloroacetyl)-N-(N'-methylenepyrrolidonyl)-2-isopropoxyaniline and N-(chloroacetyl)-N-(N'-methylenepyrrolidonyl)-2-butoxyaniline.

The specific examples which follow are presented as merely illustrative, non-limiting demonstrations of the manner in which the various compounds disclosed may be employed to achieve the useful and unexpected results when applied to turfgrasses.

EXAMPLE

The effects of the compounds of the invention on the growth of Kentucky bluegrass were evaluated in a greenhouse study. For this test, Poa praetensis L. cv. "Pennstar" was seeded in 5" fiber pots in greenhouse soil supplemented with peat moss. The pots then were placed on a greenhouse bench and allowed to grow for approximately 2 months. The grass seedlings were then trimmed to a uniform height of 6 cm. Foliar treatments of Compound A, which is N-(chloroacetyl)-N-(N'-methylenepyrrolidonyl)-2-isopropoxyaniline), chlorflurenol and maleic hydrazide were applied at rates of 4 and 2 lbs/acre with 4 pots sprayed simultaneously with 50 ml of spray solution at each concentration of test material. Additional pots were treated similarly with mefluidide at rates of 2 and 1 lb/A. A "Check" (untreated) sample was used as a control. Each treatment was replicated 4 times and the treated pots arranged on a greenhouse bench in a randomized block design. The height of the grass in each pot was measured on a weakly basis for 2 weeks. Thereafter the grass was clipped back to 6 cm, and another measurement of height was made at the end of 3 weeks. The clippings also were harvested and dry weight measurements were made.

The results are shown in Tables 1 and 2 below. In Table 1 it is seen that Compound A was particularly effective in reducing the height of growth of the grass samples without discoloration. At 4 lb/A, for example, it was as effective as chlorflurenol and maleic hydrazide, and at 2 lb/A was nearly as effective as mefluidide as well.

The data presented in Table 2 shows that Compound A caused substantial reductions in the dry matter harvested from treated turf. At 4 lb/A, the dry weight of clippings harvested from grass treated with Compound A was less than with the maleic hydrazide or mefluidide.

Although mefluidide produced the most effective height control, it also caused considerable discoloration, even at the lower rates. Discoloration was much less pronounced with Compound A. Although maleic maleic hydrazide and chlorflurenol did not cause as severe discoloration as mefluidide, they also did not provide as effective height control of the turfgrass. Accordingly, Compound A is considered as a material of choice for effective retardation of turfgrass home lawns and golf courses.

TABLE 1

Effect on the Height Growth of Potted Bluegrass (cv. "Pennstar") Seedlings.

| Test Compound | Concentration (lb/A) | Average Height (cm) | | | |
|---|---|---|---|---|---|
| | | Start | 1 Week | 2 Weeks | Re-start* | 3 Weeks |
| A | 4 | 6.0 | 12.1 | 15.0 | 6.0 | 7.3 |
| | 2 | | 11.9 | 15.8 | | 8.4 |
| Maleic Hydrazide | 4 | | 12.8 | 16.5 | | 8.9 |
| | 2 | | 13.4 | 17.9 | | 10.3 |
| Cloroflurenol | 4 | | 13.1 | 16.3 | | 8.1 |
| | 2 | | 12.6 | 16.1 | | 8.9 |
| Mefluidide | 2 | | 12.3 | 15.1 | | 7.6 |
| Check | — | | 13.9 | 18.3 | | 10.0 |

*Restart - Cut back to 6 cm.

TABLE 2

| Test Compound | Concentration (lb/A) | Dry Weight (grams) 2 Weeks |
|---|---|---|
| A | 4 | 0.64 |
| | 2 | 0.59 |
| Maleic Hydrazide | 4 | 0.84 |
| | 2 | 1.01 |
| Chloroflurenol | 4 | 0.76 |
| | 2 | 0.75 |
| Mefluidide | 2 | 0.78 |
| Check | — | 1.06 |

What is claimed is:

1. A method for retarding the growth of bluegrass which comprises applying to said bluegrass an effective growth retarding amount of N-(chloroacetyl)-N-(N'-methylenepyrrolidonyl)-2-isopropoxyaniline.

2. A method according to claim 1 wherein said amount is 1–5 lbs/acre.

* * * * *